United States Patent
Speaker et al.

(10) Patent No.: US 10,105,295 B2
(45) Date of Patent: Oct. 23, 2018

(54) MICROCAPSULES COMPRISING A WATER-IMMISCIBLE CORE AND A WALL COMPRISING THE SALT OF A LEWIS ACID AND A LEWIS BASE

(71) Applicant: CAPSULENT, Santa Cruz, CA (US)

(72) Inventors: Tycho Joseph Speaker, Santa Cruz, CA (US); Sidra Lenore Speaker, Santa Cruz, CA (US); Talia Kalei Speaker, Santa Cruz, CA (US)

(73) Assignee: Capsulent, Santa Cruz, CA (US)

( * ) Notice: Subject to any disclaimer, the term of this patent is extended or adjusted under 35 U.S.C. 154(b) by 0 days.

(21) Appl. No.: 15/682,709

(22) Filed: Aug. 22, 2017

(65) Prior Publication Data

US 2017/0348204 A1 Dec. 7, 2017

Related U.S. Application Data

(62) Division of application No. 14/893,724, filed as application No. PCT/US2014/039704 on May 28, 2014, now Pat. No. 9,744,106.

(60) Provisional application No. 61/827,972, filed on May 28, 2013.

(51) Int. Cl.

| | | |
|---|---|---|
| *A61K 9/50* | (2006.01) | |
| *A61K 8/11* | (2006.01) | |
| *A61Q 5/00* | (2006.01) | |
| *A61Q 5/12* | (2006.01) | |
| *A61K 8/65* | (2006.01) | |
| *A61K 8/73* | (2006.01) | |
| *A61K 8/92* | (2006.01) | |
| *A61K 8/49* | (2006.01) | |
| *A61K 8/41* | (2006.01) | |
| *A61K 8/891* | (2006.01) | |

(52) U.S. Cl.
CPC .............. *A61K 8/11* (2013.01); *A61K 8/416* (2013.01); *A61K 8/4993* (2013.01); *A61K 8/65* (2013.01); *A61K 8/73* (2013.01); *A61K 8/733* (2013.01); *A61K 8/737* (2013.01); *A61K 8/891* (2013.01); *A61K 8/922* (2013.01); *A61K 9/5005* (2013.01); *A61K 9/5021* (2013.01); *A61K 9/5026* (2013.01); *A61K 9/5031* (2013.01); *A61K 9/5036* (2013.01); *A61K 9/5042* (2013.01); *A61K 9/5052* (2013.01); *A61K 9/5078* (2013.01); *A61Q 5/00* (2013.01); *A61Q 5/002* (2013.01); *A61Q 5/12* (2013.01); *A61K 2800/412* (2013.01); *A61K 2800/5424* (2013.01); *A61K 2800/5426* (2013.01); *A61K 2800/614* (2013.01); *A61K 2800/652* (2013.01)

(58) Field of Classification Search
CPC .. A61K 9/5005; A61K 9/5021; A61K 9/5026; A61K 9/5031; A61K 9/5042; A61K 9/52; A61K 9/5078
See application file for complete search history.

(56) References Cited

U.S. PATENT DOCUMENTS

| | | | |
|---|---|---|---|
| 3,959,457 A | 5/1976 | Speaker et al. | |
| 4,743,583 A | 5/1988 | Speaker et al. | |
| 4,797,234 A | 1/1989 | Speaker et al. | |
| 4,917,892 A | 4/1990 | Speaker et al. | |
| 5,093,198 A | 3/1992 | Speaker et al. | |
| 5,132,117 A | 7/1992 | Speaker et al. | |
| 5,284,663 A | 2/1994 | Speaker | |
| 5,490,986 A | 2/1996 | Speaker | |
| 5,686,113 A | 11/1997 | Speaker et al. | |
| 6,251,379 B1 | 6/2001 | Omura et al. | |
| 6,270,800 B1 | 8/2001 | Speaker et al. | |
| 6,531,156 B1 * | 3/2003 | Clark ................... | A61K 9/5026 424/489 |
| 6,638,621 B2 | 10/2003 | Anderson | |
| 8,039,015 B2 | 10/2011 | Speaker | |
| 8,092,836 B2 | 1/2012 | Donath et al. | |
| 2006/0083694 A1 | 4/2006 | Kodas et al. | |
| 2006/0251603 A1 | 11/2006 | Rigoletto et al. | |
| 2008/0312581 A1 | 12/2008 | Hardy | |
| 2012/0204894 A1 | 8/2012 | Odoms | |

FOREIGN PATENT DOCUMENTS

| | | |
|---|---|---|
| CN | 101862281 A | 10/2010 |
| EP | 0299205 A1 | 1/1989 |
| WO | 2006/063030 A1 * | 6/2006 |
| WO | 2006063030 A1 | 6/2006 |
| WO | 2008080708 A1 | 7/2008 |
| WO | 2012138696 A2 | 10/2012 |

OTHER PUBLICATIONS

Extended European Search Report for European Application No. 14803977.9, dated Dec. 12, 2016—9 Pages.
Fregonesi et al., "Brazillian Oils and Butters: The Effect of Different Fatty Acid Chain Composition on Human Hair Physiochemical Properties", Mar./Apr. 2009, pp. 273-280, vol. 60(2), Journal of Cosmetic Science, Society of Cosmetic Chemists, New York, NY.
International Preliminary Report on Patentability and Written Opinion of the International Search Authority for International Application No. PCT/US2014/039704, dated Dec. 1, 2015—6 Pages.
International Search Report for International Application No. PCT/US2014/039704, dated Oct. 15, 2014—4 Pages.

(Continued)

*Primary Examiner* — Carlos A Azpuru
(74) *Attorney, Agent, or Firm* — RatnerPrestia

(57) ABSTRACT

A microcapsule suspension for treating a protein-containing surface includes droplets of a dispersed water-immiscible core phase, an aqueous continuous phase, and a wall surrounding each core phase droplet. The wall includes the salt formed from at least one Lewis base reactant and at least one Lewis acid reactant, wherein at least one Lewis base reactant or Lewis acid reactant is amphiphilic and wherein at least one Lewis acid reactant is selected from the group consisting of proteins, protein hydrolysates, charged amino acids, and water-soluble salts of any of these.

29 Claims, No Drawings

(56) References Cited

OTHER PUBLICATIONS

Kitchener et al., "Principles of Action of Polymeric Flocculants", May 1972, pp. 217-229, vol. 4(3), British Polymer Journal (abstract only).
Entire patent prosecution history of U.S. Appl. No. 14/893,724, filed Nov. 24, 2015, entitled "Products Containing Charged Polymer Complex Microcapsules and Method of Use."
European Communication for European Application No. 14 803 977.9, dated Feb. 20, 2018, 5 pages.

\* cited by examiner

MICROCAPSULES COMPRISING A WATER-IMMISCIBLE CORE AND A WALL COMPRISING THE SALT OF A LEWIS ACID AND A LEWIS BASE

This application is a division of U.S. application Ser. No. 14/893,724, filed 24 Nov. 2015, which is the U.S. National Phase filing of International Application No. PCT/US2014/039704, filed 28 May 2014, and claims priority of U.S. Application No. 61/827,972, filed 28 May 2013, the entirety of which applications are incorporated herein by reference.

FIELD OF THE INVENTION

This invention generally relates to the use of encapsulated materials, and methods of making and using products that incorporate such materials. Because the capsules described herein are generally of very small size, such products are frequently described as microcapsules. Because the microcapsules described herein are formed by forming an ionic complex of charged polymers, they are described as charged polymer complex microcapsules.

BACKGROUND OF THE INVENTION

The use of droplets or particles of an active substance incorporated in a carrier or carrier composition is well known in various arts including pharmaceutical, medical, agricultural, and many others. Typically, specific compositions provide for the application of specific active substances in a quantity or concentration appropriate to the use, and are particularly well suited to cases where the active substance itself is not easily compounded into a suitable vehicle or to facilitate controlled release of the active substance.

Among known encapsulation compositions and methods are those based on the formation of capsular walls by the reaction of a Lewis acid and a Lewis base, aligned at a droplet interface in an emulsified two-phase (generally aqueous-organic solvent) mixture, with a core material trapped in the droplet to be encapsulated. A number of such compositions and methods, and variants thereof, are disclosed in U.S. Pat. Nos. 3,959,457, 4,743,583, 4,797,234, 4,917,892, 5,093,198, 5,132,117, 5,284,663, 5,490,986, 5,686,113, 6,270,800, and 6,531,156, in which Dr. Tully Speaker is the inventor or a co-inventor and in some of which the present inventor is a co-inventor, and in U.S. Pat. No. 8,039,015, by one of the present inventors, Tycho Speaker. The Lewis acid/Lewis base reactions described in the above cited patents involve at least one ionic polymeric material, and may be described as a complexation of that material with at least one ionic component of opposite charge to form an ionic salt product. It is convenient to refer to microcapsules formed by the methods described in the Speaker patents as "charged polymer complex" microcapsules.

A plethora of other microcapsule types and compositions are known in the art, and the cited Speaker patents above describe numerous advantages in regard to the convenience of manufacture and other characteristics of the charged polymer complexes described therein. Published PCT application WO 2012/138696 teaches use of cationic polymers in a shampoo, to enhance deposition of negatively charged polyacrylate microcapsules onto hair. However, prior art does not describe compositions that exploit the properties of the charged polymer complex microcapsules described in the cited Speaker patents. Thus there is a lack of available compositions that exploit the useful qualities of the charged polymer complex encapsulated product and also provide for a means of use that realize these benefits.

SUMMARY OF THE INVENTION

In one aspect, the invention provides a method for treating a protein-containing surface, including applying to the surface a microcapsule suspension including droplets of a dispersed water-immiscible core phase, an aqueous continuous phase, and a wall surrounding each core phase droplet, the wall including the salt formed from at least one amphiphilic Lewis acid reactant or amphiphilic Lewis base reactant, and at least one corresponding Lewis base reactant or Lewis acid reactant.

In another aspect, the invention provides a microcapsule suspension for treating a protein-containing surface, the suspension including droplets of a dispersed water-immiscible core phase, an aqueous continuous phase, and a wall surrounding each core phase droplet, the wall including the salt formed from at least one amphiphilic Lewis acid reactant or amphiphilic Lewis base reactant, and at least one corresponding Lewis base reactant or Lewis acid reactant, wherein the at least one amphiphilic Lewis acid reactant includes a protein and/or a protein hydrolysate.

DETAILED DESCRIPTION OF THE INVENTION

The invention provides compositions containing charged polymer complex microcapsules, and methods of using such compositions to provide benefits to protein-containing surfaces such as hair or fur. Use of the compositions provides a primary method of treatment imparting benefit to damaged surfaces. The compositions comprise liquids that can be sprayed or otherwise dispensed onto hair, and may be left in place or rinsed away. The compositions also provide a method for decreasing damage associated with hair aging, and for preventing further damage that would normally result, thereby providing an anti-aging benefit to hair when used repeatedly. In some embodiments, the compositions are temperature-activated or heat-responsive, employing microcapsules with a core phase that undergoes a phase change at a preselected temperature. Methods of using and applying the compositions are also disclosed.

The primary method of treatment and exemplary compositions will now be described in detail, along with methods for use for each composition, followed by a description of suitable materials for use in such compositions. Where appropriate, specific benefits observed in use of these types of formulations are further described. All of the patents, patent applications and other published documents mentioned in the present application are incorporated herein by reference for all purposes.

Primary Method of Treatment

Charged polymer microcapsules (hereafter CPM) are brought into contact with a surface, for example hair, as part of an aqueous suspension. For the purposes of the present invention, essentially any method of transferring the CPM suspension to the hair is acceptable, for example, by spraying, misting or otherwise dispensing the product directly onto hair, or by dipping hair into the product, or by transferring product indirectly to hair by use of an applicator such as a comb, sponge, or brush. Other methods appropriate to transferring liquid suspensions are expected to behave similarly. After contact with the surface, the product is rinsed away, or left in place. When a fluorescent material is included in the microcapsule cores, for example, Nile Red, the microcapsules may be observed to remain deposited on the surface of the hair by examination using a fluorescence microscope. This deposition is strongly enhanced in areas of hair showing structural damage.

Effect of Treatment on Damaged Areas of Hair

Hair undergoes a variety of types of damage through normal washing and grooming activities, and is especially damaged during color treatments or treatments to alter straightness or curl. Very commonly hair damage includes loss of a portion of the fatty acid surface layer, or in areas of greater damage, loss of the superficial cuticle layer, which may expose the deeper, more fibrous layers of the hair structure. Thus exposed, these layers are prone to further damage, including longitudinal fractures, commonly known as split ends. Such split ends are commonly visible to the naked eye, as the fractured end of the hair spontaneously separates into two or more divergent sub-strands at the site of the fracture. Damage less severe than split ends may also readily be observed using various methods of microscopy, and commonly wooly or frayed regions of the keratin macrofibrils or finer structures that compose the cortex, the interior of the hair fiber, are seen where the exterior cuticle layer has been sufficiently eroded. All of these types of damage are well known to impact hair appearance and ease of grooming, and cause individual hair fibers to catch against other fibers, impeding the natural cascade or flow when the hair is moved, such as is frequently observed in children's relatively undamaged hair.

When a damaged hair, for example a split-end, is brought into contact with the compositions of the present invention, the microcapsule suspension wets the hair effectively and microcapsules can make contact with the hair by means of diffusion within the wetted film or bulk liquid phase. The liquid and the suspended microcapsules show affinity for the hair surface and particularly wet into the rough areas and fine fractures of such damaged areas. As the composition dries, the bulk phase evaporates, leaving microcapsules deposited on the surface as well as other non-volatile components optionally included in the composition, simultaneously bringing the divergent strands together again. The split end is repaired to visible integrity and tactile smoothness. Frequently it is not possible to discern without microscopic examination that the hair was ever damaged.

It is important to specify that while split-end defects are brought together and bonded by the compositions, individual adjacent hairs do not show any clumping or bonding to each other, but rather are left more free to move independently and naturally, presumably due to smoothing and surface repair, as is described below.

The repairs thus afforded are not permanent, and the damage will eventually become visible again through repeated washing and grooming. However, for a period of up to 24 hours or longer, the hair remains visibly repaired, with the duration depending upon many factors including washing, grooming, hair type, etc.

While the visible repair of the split end may be desirable for aesthetic reasons, another benefit is realized by the smoothing and anchoring of divergent macrofibrils and finer structures from the surface of damaged hair fibers. Such microscopic fiber structures readily become entangled with adjacent hair strands and further are generally known to promote transfer and buildup of static charge upon handling. By restoring smoothness to the hair through use of the compositions described herein, damage that might otherwise result from such tangling behavior is understood to be reduced and prevented, such that regular application of these products can improve overall hair quality over time. Further, application of these compositions results in immediate reduction of static flyaway, and improvement of the cascading, flowing quality characteristic of youthful, healthy hair. When applied to damaged hair, the effect is obvious and in split-head trials (treating only one side of the head), the treated side is unambiguously improved in regard to flyaway, cascading flow, ease of combing, and manageability, and is characterized by greatly improved softness to tactile touch. While generally a range of benefits may accrue from the use of the products of the present invention, particular benefit is realized in regard to split-end repair, smoothing, ease of combing, cascade and flow, color intensity, shine, breakage resistance, frizz reduction, and flyaway reduction. Performance improvement in all of these aspects is realized by the use of the products of the present invention, relative to comparable untreated hair.

Damage to hair is widely understood to beget further damage, in a self-promoting process. Damaged areas promote tangling and resistance to combing or brushing, and this resistance results in further damage to hair through stretching, breakage, and increased applied force during grooming. Such damage is widely understood to be a normal function of aging, and the concomitant loss of the qualities of youthful hair. The restoration of these youthful qualities of hair fibers, singly and individually by the products and methods described herein, and the diminution of the process of accreting new damage through continued use of these methods may be reasonably described as providing an anti-aging benefit to hair thus treated, providing a sustained and increasing return of these youthful qualities as new, undamaged hair grows longer without being damaged by attempts to groom existing damaged hair.

Mechanism of Action

Without wishing to be bound to any particular understanding of the phenomenon, it appears that the wetting of the hair surfaces and the surface tension of the composition act in concert to bring the divergent sub-strands of the split end together, and that during drying, the repair is solidified and rendered more durable. As the product becomes fully dry, the strands remain together, anchored by the microcapsules and other non-volatile components optionally included in the composition, and by the core phase that may be released from within the microcapsules upon drying.

To provide a model of activity that is common to the formulations described herein, it is convenient to describe a specific exemplar type of behavior associated with the use of CPM on surfaces. The case of hair damage involving longitudinal fracture of the hair shaft resulting in divergent sub-fibers, commonly called split-ends, is a particularly convenient case, in that results are readily observable with the naked eye, and in a short time period. When a slurry of the CPM (such as the one described in Example 1) is brought into contact with a common split-end fracture of the hair shaft, the slurry wets along the hair and further into the gap between the two sides of the fracture. As the product dries, the diverging sides of the fractured hair shaft are drawn in and become affixed to each other, in good alignment such that in representative samples of 100 such splits thus treated, all visible damage is repaired in 95 or more of the splits. Nonetheless, adjacent hair in a swatch does not become similarly affixed, and the adhesive action appears to be localized to the damaged area. This apparent repair of the defect persists even if the repaired hair is placed in 40° C. warm water with common dish detergent or shampoo or other surfactant for 36 hours or longer with no observed changes.

While the CPM slurry of Example 1 induces repair of split-ends, none of the individual components of the slurry shows this behavior. For example, the same quantity of sodium alginate in a similar volume of water does not produce a split end repair in the absence of the dispersed phase and quaternary amine. Similarly the emulsion component alone does not, nor does the equivalent quaternary amine solution. Combined as taught in the present invention, however, these components act together to produce the repairing action. Moreover, the repair action is observed even upon aqueous dilution of the product of Example 1 by 100-fold or more.

Without wishing to be bound to any particular interpretation or model, we nonetheless propose the following working hypothesis. The wall material of the CPM contains at least one polyfunctional ionic polymer material (i.e., one with multiple charged sites), with charged moieties spaced at intervals along a polymeric chain, which is precipitated by complexation with an oppositely charged partner counterion to form the CPM wall. When this happens, and particularly when the partner counterions are polyfunctional, some residual charged sites are believed to remain uncomplexed. That is, some fraction of the charged regions of both the primary and partner counterion materials is reasonably expected to remain un-neutralized due to steric effects and misalignment in the spacing of one group of charges and the corresponding group of spaced counter-charges on other molecules as they are precipitated to form the CPM wall structure. Therefore, available charged cationic and/or anionic moieties are believed to remain after formation of the CPM, and these are understood to be an important part of the observed behavior with respect to surfaces such as the damaged area of a hair shaft, which is known to be hydrophilic and rich in negative charge as compared to intact hair which is hydrophobic and relatively charge neutral. The relatively high charge and hydrophilicity of damaged hair as compared to relatively hydrophobic undamaged hair is also understood to contribute to the localized enriched deposition of the microcapsules at damaged areas.

We propose that one explanation for the split-end repair activity of the CPM suspension is that the charged surface of the CPMs may interact strongly with the charged surface of the damaged hair protein structures, forming a layer of CPMs that blankets the damaged area.

Further, CPMs in aqueous suspensions in a drying droplet are observed to exhibit rafting behavior, avoiding the drying edge as the droplet dries upon a surface, presumably driven by the thermodynamic energy cost associated with dewetting and drying the charged exterior of the CPM.

Macroscopic CPMs made with excess wall materials can be made, for example those taught in Speaker patent U.S. Pat. No. 6,531,156, and the resulting walled capsules may be studied as related to the capsules of the present invention. While wet, such capsules are significantly elastic and deformable, but if they are dried on a surface, they adhere to each other strongly. In the present invention it is observed that concentrated slurries of CPMs will dry on a surface to form a tough and cohesive film or network, similar to the macroscopic version described above. However, the interior oil phase of the CPMs is released as the material dries, making the dried polymer films difficult to re-wet or resuspend.

In the light of these macroscopic observations, it is reasonable to suggest that the CPMs not only interact strongly with the damaged surface of the split-end, but further raft together as the hair dries, concentrating a population of CPMs in the gap between the damaged pieces. As this population dries, interaction between individual CPMs becomes strong and these can form a structural matrix similar to the films observed to form on a flat surface. Because the interior payload of any individual CPM is very high, above 99.5% by weight of each CPM, as this interior is released, the remaining drying wall material surrounds much less volume, much as a rubber balloon occupies much less space when it is deflated. Thus aggregation of the particles may occur during the drying process, to form a matrix of walled "cells" consisting of the microcapsules. These cells then further exude their payloads as the product evaporates to dryness, flattening the matrix and developing tensile force on points of attachment.

Thus the CPM are thought to self-assemble within the gap space of the split-end to form a 3-dimensional matrix. The CPM release their contents as they dry, and shrink during that process, which causes the split-end to come together in a zipper-like fashion. The released CPM contents also wet or seal the densified matrix of CPM wall material with a protective oil layer that prevents facile resuspension or washout of the deposited material.

Importantly, the repaired divergent parts of each hair are observed to be well-aligned, leaving the hair with apparent structural integrity. This is in contrast to what may be observed if hairs are "glued" with ordinary adhesive materials. Rather, the repair is normally visibly indistinguishable from native, undamaged hair. A further benefit realized by the present invention is that whereas a standard adhesive would leave any adjacent hair tacky and promote tangling, the compositions of the present invention leave adjacent hairs soft, non-tacky, and are observed to inhibit subsequent tangling.

Selective Deposition

The CPM suspensions of the present invention appear to deposit selectively and preferentially at sites of hair damage, most especially in areas with observable physical damage, such as split ends and frayed areas. Without wishing to be bound to a particular framework of understanding, several effects appear to be relevant to this selective deposition. First, the CPM are understood to possess substantial surface ionic charge, both cationic and anionic. This external charge is further understood to promote electrostatic interaction between the CPM and anionic sites on damaged hair, while the hydrophobic surface of healthy intact hair provides no basis for attraction to the CPM. Further, in the compositions of the present invention, the CPM are dispersed in an aqueous continuous phase that is repelled by the hydrophobic surface of healthy intact hair, but which wets very efficiently into the topology of fractures and roughened areas associated with physical hair damage. Combined, these effects are understood to concentrate the CPM at damage sites, while minimizing CPM populations adsorbed to the smooth hydrophobic surfaces presented by intact healthy hair. Because CPM are selectively associated with damage sites, a product comprising a slurry of suspended CPM may be applied to an entire head of hair, and yet be preferentially deposited upon damaged areas of hair. Similarly, CPM are understood to be easily rinsed away from undamaged hair surfaces while deposition of CPM upon the anionic sites presented by damaged hair is understood to be robust and not easily rinsed away.

Stabilized Compositions

The microcapsule suspensions described in the present invention are not necessarily of the same density as the continuous phase of a product, and therefore to avoid creaming or settling over time, compositions may be improved by inclusion of one or more suspending agents in the aqueous continuous phase. The suspending agent(s) is/are added after formation of the microcapsule walls and are not a part thereof. Exemplary suitable suspending agents are selected from the group consisting of gellan gum, alginate, carboxymethylcellulose, carrageenan, locust bean gum, starch, guar gum, pectin, arabic acid, hydroxypropyl methylcellulose, carbomer, and chemically modified versions of any of these materials.

Typically for a spray-on product, suspending agents such as water soluble salts of alginate, carrageenan, carboxymethylcellulose, microcrystalline cellulose, and/or other hydrocolloids such as gellan gum, guar gum, locust bean gum, pectin, starch, xanthan gum, as well as chemically modified or derivatized forms of these gums, or any other material with similar properties, singly or in combination are useful for this purpose, dissolved in the aqueous continuous phase. One suitable composition is a composite system including gellan gum at about 0.01%-0.50%, preferably 0.05%-0.1%, and sodium alginate at about 0.01%-5.00%, preferably 0.1% to 0.5%. Another suitable composite system includes locust bean gum at about 0.01%-0.50%, preferably 0.05%-0.15%, xanthan gum at about 0.01%-0.50%, preferably 0.05%-0.15%, and sodium alginate at about 0.01%-5.00%, preferably 0.05%-0.1%. Optimal use levels vary depending upon the source and grade of suspending agents incorporated. These systems provide sprayability and viscosity appropriate to a spray-on, leave-in hair product. A model product incorporating these elements is presented in Example 2. Because damaged areas of hair are generally known to be rich in anionic surface species, it might be expected that the inclusion of anionic species in the continuous phase would serve to dilute and inhibit interactions between the CPM and damaged areas. Surprisingly, the presence of anionic dissolved solid materials (e.g., alginates) enhances the rapidity and durability of the split-end repairs achieved by application of the material of Example 2. Without being bound to an interpretation, it seems likely that the benefit of the dissolved anionic polymers may be in part due to colloid charge effects and in part due to viscosity changes during product drying due to the dissolved solids content. As the product dries, the extra polymer material may assist in development of strong particle-particle adhesion and a more robust, patch-like repair.

Additional Benefits

While a primary benefit to hair is understood to be the repair activity of the CPM, and re-integration of divergent fibrils and damaged areas of hair, a number of aspects of the hair generally are improved. While these aspects are understood to be associated with and resulting from the primary effects of the repairing action, each is of value in its own right. Some of these qualities may be a direct result of anchoring and reattachment of divergent fibrils and structures, including cuticle scales. However, integral with this structural repair is the release of benefit agents, including oils, which may work in concert with the CPM wall material or independently.

Smoothing of the hair and improvement of softness to touch are immediately noticeable qualities associated with use of the CPM, and understood to be in part due to a reduction of surface roughness of individual hair fibers as well as repair of major structural damage. Understood to be related to tactile smoothness, ease of combing is also enhanced, with a noticeable reduction in tangling behavior as the hair glides more easily through the comb.

Further related to smoothness and reduced friction between adjacent hairs, cascade and flow of hair following displacement is observed to be dramatically improved.

As surface roughness is reduced, it is understood that corresponding diffuse optical scattering is also reduced, leading to an intensification of visible hair coloration and more translucent, richer coloration of individual hairs under microscopic observation. Shine, associated with enhanced color intensity and loss of diffuse light scattering, is noticeably enhanced. Shine may be described as the difference between the intensity of observed specular reflection and adjacent areas of hair not reflecting light toward the observer. As the diffuse light scatter due to roughness is reduced, the contrast between visible specular reflection and adjacent dark areas is increased, making shine more intense and noticeable.

In addition to effects associated with reduction in hair roughness, noticeable strengthening of hair and increased resistance to breakage is observed. Without being bound to a particular understanding of why hair is strengthened, it is reasonable to assume that sealing of fracture points plays a role, but that benefit oils released by the CPM during drying may produce not only lubricity, but plasticization of the keratinaceous filaments and exterior layers of individual hairs, leading to observed improvement in breakage resistance.

A further benefit observed with application of products containing CPM is a marked reduction in frizz and unruly hair. Without wishing to be bound to a particular mechanism by which frizz-reduction occurs, it is reasonable to assume that both the high charge density of the CPM wall materials and the release of benefit oils might play roles in this phenomenon, as the dense surface charge distribution of the CPM is expected to combat electrostatic effects while plasticization of the hair by oils may relax curl radius.

Lastly, flyaway, individual hairs that do not lay evenly, but extend at an angle divergent to the overall population of hair are rapidly and substantially reduced by application of products containing CPM. Flyaway is generally attributed to electrostatic charging of the hair. The high density of surface charge presented by the CPM wall is understood to play a strong role in dissipating static charge in the hair. While nominally the CPM have zero net charge, they exhibit a plethora of both positively and negatively charged moieties decorating the exterior wall. Without being bound to any interpretation, this high charge density is understood to effectively neutralize the relatively much smaller accumulated charge on the surface of individual hairs upon contact, leading to flyaway reduction. It is important to state that the benefits described in regard to split-end repair, smoothing, ease of combing, cascade and flow, color intensity, shine, breakage resistance, frizz reduction, and flyaway reduction are not merely momentary effects, but may persist for many hours or days after application of a product containing CPM.

Additional Components in the Continuous Phase

The microcapsule suspensions described herein may also be improved by addition of other components dissolved or suspended in the continuous phase, intended to impart additional benefits to the overall product Normally compositions used in Personal Care will include fragrances, preservatives, rheology modifiers and the like. Frequently compositions intended for use on hair will further include polymers intended to impart curl, to fix hair styles in place, to give structure to the hair, etc. The microcapsules of the present invention can be combined with these and other types of hair products, including styling aids, shampoos, conditioners, pre-shampoos, and detanglers, to impart additional benefit to such compositions. The compositions of the present invention may therefore be further improved by addition of other materials that may not specifically interact with the microcapsule walls, for instance fragrances, dyes or pigments, polyvinyl alcohol, glycerin, acrylates copolymers, acids and bases used to adjust pH, and so on.

Microcapsule Wall Materials

As taught in Speaker patent U.S. Pat. No. 8,039,015, a wide variety of combinations of Lewis acid and Lewis base wall materials may be effectively used to produce microcapsules, and any of these may be used according to the present invention. Exemplary suitable Lewis acids include the following Lewis acids and their anions and water-soluble salts: alginic acid, arabic acid, carboxymethylcellulose, carbomers and related polymers and block copolymers bearing carboxylic acid moieties, hyaluronic acid, gellan gum, pectin, xanthan gum, and water-soluble proteins and/or water-soluble full or partial protein hydrolysates. Suitable exemplary proteins include albumin and collagen. Suitable partially hydrolyzed proteins include hydrolysates of keratin, milk, rice, soy, silk, and/or wheat proteins. Generally, polymeric materials of molecular weight above 1000 amu presenting at least two carboxylic acid reactive groups, or combinations of these materials, are suitable Lewis acid reactants.

Lewis base reactants producing microcapsules suitable for use in the present invention include those taught in Speaker patent U.S. Pat. No. 8,039,015 and comprise the following Lewis bases, anions, and their water-soluble salts: benzalkonium, cetylpyridinium, chitosan, cocodimonium hydroxypropyl hydrolyzed keratin, cocoglucosides hydroxypropyl, hydroxypropyltrimonium hydrolyzed wheat protein, hydroxypropyl oxidized starch PG-trimonium, PEG-3 dioleylamidoethylmonium methosulfate, laurdimoniumhydroxypropyl decylglucosides, polyquaternium-10, polyquaternium-11, polyquaternium-78, polyquaternium-80, polyquaternium-81, polyquaternium-88, polyquaternium-101, quaternium-79 hydrolyzed silk protein, silicone quaternium-17, silicone quaternium-8, starch hydroxypropyltrimonium, steardimonium hydroxyethylcellulose, steardimonium hydroxypropyl panthenyl PEG-7 dimethicone, cocodimonium hydroxyethylcellulose, polyvinylamine and generally, any water-soluble quaternary amine or similar Lewis base capable of forming a salt with the carboxylic acid moieties of the Lewis acids described above, or combinations of any of these materials.

Capsule wall materials may further additionally comprise a wide variety of materials that will react with the Lewis acid or Lewis base component. These materials include proteins, partially hydrolyzed proteins, charged amino acids and any of these materials further linked to other compounds that can form salts with the wall materials, some representative examples of which are the quaternized hydrolyzed proteins listed in the exemplar Lewis bases, above. These materials may impart particular biological compatibility or additional reactive sites or other desirable properties to the wall. Water-soluble proteins may be used as components of the CPM wall if they can be precipitated by the Lewis base component of the wall. For example, ovalbumin is both readily solubilized and rapidly precipitated by a number of the Lewis bases described. A useful CPM may be formed by substituting ovalbumin for part or all of the alginate component in Example 1. Similar CPM compositions may be formed using other water-soluble proteins precipitated by Lewis base components. Some proteins may not be highly water-soluble, but nonetheless hydrolysates of such proteins exhibiting higher water solubility may be incorporated into useful CPM compositions. For example, hydrolyzed wool keratin protein in aqueous solution readily precipitates in the presence of sufficient polyquaternium-10, but does not itself form a robust microcapsule wall (presumably because the hydrolysis product chain length is too short to form a matted structure of overlapping sterically entangled precipitated molecules characteristic of the walls of Speaker patent U.S. Pat. No. 8,039,015. However, inclusion of the same hydrolyzed protein in the wall composition as shown in Example 4 in conjunction with a longer chain Lewis acid component sodium alginate, forms a robust wall suitable for use in a hair product. As the product is useful to address damage to hair, inclusion of hydrolyzed protein similar to the hair itself, for example hydrolyzed wool keratin, may reasonably be expected to impart additional compatibility with the surface of hair, as the hydrolysis products are similar in composition to the proteins exposed at damaged sites. While essentially any hydrolyzed protein may be useful in forming such composite wall structures, known useful materials include commercially available hydrolysates of keratin, collagen, silk, rice, soy, wheat, and milk proteins. It will be apparent to those familiar with protein solubility that solution pH and ionic strength exert a strong effect on protein solubility and ionization states, and that pH and ionic strength may be manipulated to promote solubilization of a particular protein and to enhance precipitation interactions with the exemplar Lewis bases described above to support formation of a useful CPM.

Microcapsule Core Materials

As taught in Speaker patent U.S. Pat. No. 8,039,015, a wide variety of materials may be incorporated in the interior, encapsulated core of the microcapsules described therein. The principal requirement limiting such materials is that the core material as a whole must form a distinct immiscible phase separate from the continuous aqueous phase into which wall materials are introduced. Any of a wide variety of oils and oil-miscible materials known and claimed to provide hair benefit are suitable for inclusion in the core phase of the microcapsules described herein. Useful core phases include but are not limited to: argan (*Argania spinosa* L.) oil, baobab (*Adansonia digitata*) seed oil, broccoli (*Brassica oleracea*) seed oil, mango (*Mangifera indica* and related) oil, moringa (*Moringa oleifera*) seed oil, palm (*Elaeis guineensis* and related) oil, tea (*Camellia sinensis*) seed oil, marula (*Sclerocarya birrea*) nut oil, shea (*Vitellaria paradoxa*) oil, tamanu (*Calophyllum inophyllum*) oil, common food oils, and other triglycerides or blends thereof, acetyltributyl citrate and other simple esters or blends thereof, icosane and other liquid or liquefiable alkanes or blends thereof, and dimethicone and other silicone fluids or blends thereof. Liquefiable alkanes include those with a melting point of at least around 35° C. and at most 200° C., or at most 100° C., or at most 60° C. Additionally, any permutations of the identified core material types can potentially be co-solubilized to form similar useful compositions. Further, diverse additional active agents may be solubilized within the core phase, further extending the range of benefit agents that may be incorporated. For example, materials that provide ultraviolet protection, or antioxidant protection, improved wetting or adhesion to hair may be incorporated.

Secondary agents that may be solubilized are diverse, but specific examples are provided as illustrative of the general concept Octylmethoxycinnamate (Galaxy 2932, Galaxy Surfactants Inc. Navi Mumbai) is miscible in all proportions with a variety of triglycerides and other esters and may be readily incorporated into a CPM core phase consisting of any of the triglyceride materials mentioned above to produce a product that provides a UV-protective benefit for hair or hair colorings. Similarly, tocopherol (vitamin E) or esters of tocopherol are miscible in triglycerides and such a mixture may be included in a CPM product, delivering antioxidant activity in the context of the CPM system. Similarly, hydrogenated castor oil/sebacic acid copolymer (Crodabond CSA, Croda Inc., Edison, N.J.) may be included in the core phase of a CPM product to produce improved adhesion in the repair. These examples serve to illustrate that a great variety of additional materials may be usefully incorporated within the core phase of the microcapsules of the present invention.

Of particular interest in the present invention is the behavior of three groups of materials, esters (including triglycerides), silicones, and alkanes. Use of a product according to the present invention that contains microcapsules with a core phase containing an ester will repair split ends very effectively. In contrast, use of a product that is identical in composition except for the replacement of the ester-containing core with a core comprising a silicone oil or an alkane will not effectively repair split ends. If a composite product is formed by combining at least 30% of an ester-core CPM population with 70% or less of a CPM population containing a silicone or an alkane, or a combination of such products, the resulting product comprising distinct populations of microcapsules, one with ester cores and others with silicone and/or cores, the resulting combined product is observed to be effective in repairing split ends, similar to the ester-only product. While for purposes of description it is useful to describe materials that fall specifically within one of the three groups, esters, silicones, and alkanes, it will be obvious to one of ordinary familiarity with materials in common, current use in the Personal Care industry that some materials cross these nominal boundaries, for example functionalized silicones bearing alkane or ester moieties such as dimethiconol behenate (Pecosil D B, Phoenix Chemical, Somerville, N.J.), phenyl trimethicone (556 Cosmetic Fluid, Dow Corning Midland, Mich.) and many others. These materials may be readily included within the core of the CPM to provide benefits associated with more than one of the groups described above.

Without wishing to be bound to a particular interpretation of the observed behavior, it is reasonable to propose that the effective repair observed in the present invention associated with ester-containing cores and the non-repair observed using silicone or alkane cores is related to the relative polarity of these materials, which may interact with the repair process by altering wetting behavior, lubricity of the product during drying, surface tension of the product, or other qualities that prevent a silicone-only product from repairing split ends.

Because silicones are very commonly used in commercial products to impart desirable qualities to hair, it can be useful to include silicone-core microcapsules in the hair products described herein, to gain the benefits of silicone while retaining the repairing benefits of the ester compositions, as well as other benefits such oils may impart Thus a benefit agent in the present composition need not be specifically associated with a hair-repair function to be a useful and desirable part of the overall composition.

Limitations on Relative Proportions of Wall Components

It will be readily apparent to those familiar with polymers that in all but very specialized applications, the terms "molecular weight" and "molar concentration" refer to "average molecular weight" and "approximate molar concentration" as practically applied. Any particular sample of a polymer is likely to contain a wide distribution of molecules of different chain lengths, and even two samples drawn from the same batch of prepared material may contain substantially different relative populations of polymer chain lengths. Therefore while effort is made in the present invention to define limiting aspects in regard to absolute concentrations and quantities, in practical terms the precision with which this can be expressed in quantitative terms is limited.

Similarly, in regard to discussion of the quantities of microcapsules used in products described herein, the microcapsules formed by the methods of the aforementioned Speaker patents are formed as a distribution of sizes, and even two samples of a single batch of microcapsules thus formed may contain substantially different sizes and therefore numbers of particles. Therefore it is difficult to assign exact quantitative limits to the numbers of particles or levels of use in the present invention.

One factor that limits the levels of wall reagent used in the present invention may be readily observed to be the quantity of Lewis base materials used relative to the quantity of Lewis acid materials used. Some Lewis bases, for instance benzalkonium chloride (BZK), readily form microcapsule walls with a Lewis acid wall reactant partner, such as sodium carboxymethylcellulose (CMC), as taught in Speaker patent U.S. Pat. No. 8,039,015. The resulting homogeneous, milky suspension of microcapsules produced as in Example 3 is found to be very effective in repair of split-end hair damage, for instance. However, if the quantity of BZK in the example is increased three-fold, for instance by adding the same volume of a higher concentration of BZK, a distinct aggregation of the product is observed, visually similar to the formation of curds in soured milk. The aggregated product is no longer useful in regard to the repair of hair damage, with respect to the present invention. Therefore there exists a distinct upper limit of Lewis base wall reactant content above which a useful product is not formed. This range is defined as the range within which the Lewis base wall reactant does not produce aggregation of the microcapsules.

Without wishing to be bound to any particular interpretation, it is understood from Speaker patent U.S. Pat. No. 8,039,015 that as the first amphiphilic wall-forming reactant accumulates at the phase interface of an oil droplet suspended in an aqueous continuous phase, hydrophobic regions of the reactant orient toward the interior of the droplet and hydrophilic regions of the reactant orient to remain in contact with the continuous phase. Introduction of the second wall-forming reactant to the continuous phase results in formation of the salt product of the two wall reactants at the phase interface. Before introduction of the second wall-reactant, the suspended droplet, cloaked in a layer of the first reactant, resembles a colloidal suspension of charged particles, and the first reactant further plays the role of a protective colloid. Such systems may be sensitized, and rapidly flocculated in some cases if sufficient counterion is added to neutralize surface charge. This effect has been seen in many systems, and for instance dilute polystyrene latexes, possessing carboxyl groups, are rapidly flocculated by low molecular weight polyamines, approximately as the particle charge is neutralized [Kitchener, J. A. "Principles of action of polymeric flocculants." British Polymer Journal 4.3 (1972): 217-229]. It seems likely that a similar effect is responsible for the flocculation observed in some microcapsule suspensions when excess Lewis base is introduced.

Nonetheless, not all of the Lewis bases described will cause flocculation, even at high concentrations. It is understood that long polymer chains decorated with Lewis base moieties will interact with similar polyfunctional Lewis acids at the phase interface of a droplet in the compositions of the present invention. However, due to steric effects and mismatches in the spacing of the charged groups on both sets of molecules, it is statistically unlikely that every charged group on each polymeric molecule will localize so as to neutralize every group of opposite charge on the complementary wall-forming reactant pair. Therefore, many of the polyanion/polycation systems of the present invention are not observed to form flocculates in any relative proportion, and are observed to form useful products for hair treatments in any relative proportion tested.

The present invention comprises a wide variety of systems including many single- and multiple-pairings and permutations of Lewis acid-Lewis base wall-forming reactants. Generally, all of these systems are suitable for inclusion in the compositions of the present invention, except those systems in which excess Lewis base causes flocculation, which are most frequently found to be systems in which the Lewis base is of relatively low molecular weight and possesses only a single cationic group per molecule.

Cationic Compositions

Having noted above that excess cationic components can destabilize the microcapsules by flocculation, and further that anionic polymers such as alginates appear to provide a synergistic benefit in hair-repair activity of the present compositions, it is also noteworthy that cationic species can serve to inhibit the repair activity in, for instance, some hair conditioner compositions. However, such activity is readily mitigated by inclusion of low-charge density polymers. For example, a suspension of CPM in a 1% solution of cetyltrimethylammonium chloride (CTK) a common quaternary amine in hair compositions, will not produce the durable repair observed in the product of Example 2. However, inclusion of low charge-density materials such as locust bean gum and/or a low substitution quaternized guar gum such as Jaguar C-13S (guar hydroxypropyl trimonium chloride, Solvay, Brussels, Belgium), at a 1% use level restore repair activity. Without being bound to a particular interpretation, it is understood that low-charge density materials produce a charge shielding effect that stabilizes local charges from strong interactions in a manner analogous to colloid stabilization by similar materials as commonly practiced in the formulation of pharmaceutical suspensions, for example. By judicious exploitation of this effect, it is possible to include useful quantities of cationic materials in the present compositions while yet retaining hair repair activity as well as product stability. A representative cationic conditioner composition that shows good split end repair activity is given in Example 5, below.

Use Levels of Microcapsules

The microcapsule suspensions of the present invention are found to be effective at producing a visible repair of split ends at use low use levels. For example the product of Example 1, below, effectively repairs split-end defects when diluted with water such that the dispersed, encapsulated phase comprises only 0.1% of the product. Nonetheless it is understood that higher use levels in products are expected to improve the net beneficial effect imparted by the product, and that there is no limiting factor other than the inconvenience of manufacturing very highly loaded encapsulated slurries, either directly or by concentrating an existing slurry.

In contrast to the effective split-end repair produced by the diluted product as described in the preceding paragraph, none of the component elements of the product, comprising equivalent alginate solutions, quaternary amine solutions, or oil emulsions alone is effective in producing a split-end repair, indicating that the complete microcapsule formulation alone is specifically effective in this regard.

While a single use of a product containing less than 0.1% of encapsulated phase may not reliably produce a visually evident repair of a split-end fracture in hair, it is nonetheless understood that smaller defects not visible to the naked eye may be repaired at lower use levels, and that the split-end fracture may be nonetheless partially repaired or ameliorated by use of a low-concentration product. Therefore so long as any microcapsules are present in a composition similar to those described in the present invention, these are arguably sufficient to contribute to the efficacy of such a product, and no use level is so low as to be excluded from this beneficial range.

Temperature-Dependent Microcapsules

Many common hair treatments involve changing the temperature of hair, for example, blow-drying or flat-ironing treatments heat the hair, after which the hair is cooled again. When the compositions and methods of the present invention include microcapsules comprising a core material that undergoes a temperature induced phase transition such as melting, solidification, or evaporation, the hair-repair behavior of the product can be enhanced, and a heat-protective quality may also be realized.

By including for example a waxy or resinous component or any other material in the core phase, such that the core phase as a whole is solid at normal body temperature, but is liquefied when the hair is heated with a blow dryer, iron, or other heated implement, the release of the core phase from the capsules can be controlled to occur only when and where sufficient heat is applied. For instance, a core comprising 95% argan oil (*Argania spinosa* L. kernel oil) and 5% carnauba wax exists as a firm solid at 37° C. body temperature, but is readily liquefied under the hot air flow of a typical hair dryer from a distance of one foot, similar to the conditions experienced by hair when dried in this manner. When samples of hair with split-ends are treated with such a composition, for example the one described in Example 6, visual inspection shows that the split end is repaired while microscopic inspection reveals discrete capsules sparsely adherent to the surface of the hair and aggregated capsules filling the region of the split end damage. Thus, formation of a visible repair does not seem to be solely dependent upon having the majority of capsules release their contents fully. When the same sample is inspected after being heated in the flow of a hair dryer, the capsules are no longer observable as discrete spheres, but the spherical structures have apparently flattened and the core material is observed as a diffuse coating continuous within and around the repaired split end. The damaged hair macrofibrils and split fibers further appear to be even more conformal and less divergent than before heating. At normal hair temperature, the core phase is solid, and the repaired area, now sealed by this released core material is understood to be more physically robust and less prone to removal or washing away, as compared to a repair that does not include a solidified component Similar core materials with temperature-selectable melting points can be composed using resins, polymers, and other materials well known to influence the gellation and/or solidification of oils and waxes. Core compositions suitable for providing the aforementioned effects typically have a phase transition of at least 37° C., or at least 45° C., and at most 100° C., or at most 65° C.

Cores that undergo phase transition can be used to trigger heat-activated release of benefit agents, or selective release of specific benefit agents by heating different areas of the hair to different temperatures. For example a product comprising the normally-solid-core microcapsule described above can be combined with a product comprising normally-liquid-core microcapsules, such that the benefits ascribed to the liquid-core microcapsules are delivered to the entire length of the hair fiber, while the more durable repair associated with the solid core capsules is only realized at the ends of the hair, when these are selectively heated using a blow-dryer. A further benefit realized by use of materials that undergo heating-induced phase transitions is that such materials may additionally provide thermal protection. In particular, if materials are selected to include those with melting points between of at least around 35° C. and at most 200° C., or at most 100° C., or at most 60° C., and having relatively high latent heat of fusion, a specific thermal protection benefit may be further realized, as such materials will serve to prevent overheating of the hair. While a broad variety of materials exist that will provide such benefit, particularly suitable thermal properties are associated with paraffins of 12 to 24 carbon chain lengths.

Suitable materials for inclusion in the core phase that are useful to create a temperature-selectable phase transition in the core phase include but are not limited to: waxes such as hydrogenated triglycerides, acacia wax, stearin, candelilla wax, carnauba wax, beeswax, paraffin, fatty alcohols, silicone wax, ozokerite, resins such as shellac and rosin, polymers such as polyamides, copolymers of vinylpyrrolidone and long-chain olefins such as those marketed as Ganex V220 (VP/Eicosene Copolymer, Ashland Chemical, Dublin, Ohio), and combinations of these and/or any other material that causes a temperature-reversible phase change in an oil phase.

EXAMPLES

Example 1. Charged Polymer Microcapsules Containing Argan Oil

A core phase consisting of 10.000 grams argan kernel oil (Earth Supplied Products, Naples, Fla.) is dispersed in 50.000 grams of a 0.060% weight aqueous solution of sodium alginate further containing 0.250 grams sorbitan monooleate (Jeechem S M L, Jeen Chemical, Fairfield, N.J.) and 0.250 grams polysorbate 20 (Ritabate 20, Rita Corp., Crystal Lake, Ill.) using a rotor-stator homogenizer to make a fine white emulsion. The emulsion is stirred during gradual addition of 39.500 grams of an aqueous solution containing 0.025% polyquaternium-10 (U-CARE JR 400, Dow Chemical Co., Midland Mich.). The product thus formed produces consistent repair of split ends when the hair is stroked through the suspension.

Example 2. Spray-on Product Containing CPM for Repair of Hair Damage, Including a Stabilizing Suspending Agent A continuous phase comprising 0.1% gellan gum in water is prepared. This continuous phase is used to dilute the product of Example 1 in a 1:1 ratio. The product thus formed produces consistent repair of split ends when the hair is stroked through the suspension or the when the product is applied as an atomized mist.

Example 3. CPM Sensitization and Flocculation

A core phase consisting of 10.000 grams argan kernel oil (Earth Supplied Products, Naples, Fla.) is dispersed in 50.000 grams of a 0.1% weight aqueous solution of sodium alginate further containing 0.250 grams sorbitan monooleate (Jeechem S M L, Jeen Chemical, Fairfield, N.J.) and 0.250 grams polysorbate 20 (Ritabate 20, Rita Corp., Crystal Lake, Ill.) using a rotor-stator homogenizer to make a fine white emulsion. The emulsion is stirred while adding 38.500 grams of an aqueous solution containing 0.050% benzalkonium chloride. The suspension remains milky and homogeneous. The product thus formed produces consistent repair of split ends when the hair is stroked through the suspension.

To this milky suspension, an additional aliquot of 1.500 gram of a 1.000% aqueous solution of benzalkonium chloride is further added. The suspension rapidly sensitizes, assuming a characteristic granular appearance, substantially clarifying the continuous phase, as the microcapsules form a curd-like mass at the product surface, with concomitant liberation of a portion of the core phase. This product does not exhibit split end repair capability.

Example 4. Protein-Containing CPM

A core phase consisting of 10.000 grams argan kernel oil (Earth Supplied Products, Naples, Fla.) is dispersed in 45.900 grams of a 0.060% weight aqueous solution of sodium alginate further containing 0.100 grams of hydrolyzed wool keratin (KERA-TEIN V, Tri-K Industries, Denville, N.J.), 0.250 grams sorbitan monooleate (Jeechem SML, Jeen Chemical, Fairfield, N.J.) and 0.250 grams polysorbate 20 (Ritabate 20, Rita Corp., Crystal Lake, Ill.) using a rotor-stator homogenizer to make a fine white emulsion. The emulsion is stirred during gradual addition of 39.000 grams of an aqueous solution containing 0.025% polyquaternium-10 (U-CARE JR 400, Dow Chemical Co., Midland Mich.). The product thus formed produces consistent repair of split ends when the hair is stroked through the suspension.

Example 5. Hair-Repairing Cationic Conditioner

A 50.000 gram sample of an aqueous solution consisting of 1.0% Jaguar C-135 (Solvay), 1.6% Locust bean gum, 1.6% Xanthan gum is prepared, by combining separately prepared solutions of appropriate concentrations, to form solution A. To this solution is added 3.000 grams of a microencapsulated argan kernel oil, similar to that described in Example 1, above. In a separate vessel, 2.000 grams of cetyl alcohol are dispersed in 30.000 grams of a 75° C. aqueous solution of 0.5% behentrimonium chloride to form solution B. Solution A and solution B are combined and stirred to completely mix. To the combined product, a third solution, C, is added consisting of 4.000 grams of a 2.0% cetrimonium chloride solution and 1.000 gram of a 0.5% polyquaternium-80 solution, followed by 12.000 grams of water to complete the example formulation. When a split-end is washed in a 5.0% aqueous sodium lauryl sulfate solution, subsequently rinsed with this example product, and finally rinsed with water and dried, this product is observed to repair hair effectively while providing the additional rinse-out feel and detangling associated with cationic conditioners.

Example 6. Temperature-Triggered CPM

A core phase consisting of 8.000 grams argan kernel oil (Earth Supplied Products, Naples, Fla.) and 2.000 grams candelilla wax (Earth Supplied Products, Naples, Fla.) is prepared by heating to 90° C., then cooling to 65° C. The core phase is dispersed in 45.900 grams of a 0.060% weight aqueous solution of sodium alginate further containing 0.100 grams of hydrolyzed wool keratin (KERA-TEIN V, Tri-K Industries, Denville, N.J.), 0.250 grams sorbitan monooleate (Jeechem SML, Jeen Chemical, Fairfield, N.J.) and 0.250 grams polysorbate 20 (Ritabate 20, Rita Corp., Crystal Lake, Ill.) maintained at 65° C., and is dispersed using a rotor-stator homogenizer to make a fine white emulsion. The emulsion is stirred during gradual addition of 39.000 grams of an aqueous solution containing 0.025% polyquaternium-10 (U-CARE JR 400, Dow Chemical Co., Midland Mich.). The product is cooled and combined with an equal volume of 0.1% aqueous gellan gum as a suspending agent.

Example 7. Composite Hair Product for Multiple Benefits

Microcapsules as recited in Example 1 above are prepared, substituting other oils for argan oil in the core phase, with no other alteration to the process except heating as required to melt the core phase, to generate microcapsules containing dimethicone (SPI 350, Silicones Plus, Arlington, Tex.), shea olein (*Vitellaria paradoxa* nut oil, Earth Supplied Products, Naples Fla.), and mango butter (hydrogenated *Mangifera indica* L. seed oil, Earth Supplied Products, Naples Fla.). The products are each combined with equal volumes of a 0.1% gellan gum Kelcogel CG-HA, CP Kelco Atlanta, Ga.) solution for product stability. Keratin-wall argan microcapsules as recited in Example 4 are also prepared and similarly stabilized. The heat-fusible argan CPM of Example 5 are prepared as well. These CPM populations are combined to form a composite product comprising: 20.000 grams dimethicone CPM, 10.000 grams shea olein CPM, 4.000 grams keratin-wall argan microcapsules, 4.000 grams heat-fusible argan CPM, and 2.000 grams mango butter CPM. This composite product is diluted by addition of 30.000 grams of a 0.100% gellan gum aqueous solution and 25.000 grams of a 1.000% sodium alginate (Protanal 2340, FMC Corp., Philadelphia, Pa.) aqueous solution, and 5.000 grams of a 1.000% carrageenan (Viscarin PC-109, FMC Corp., Philadelphia, Pa.) aqueous solution. The resulting sprayable product provides split-end repair and enhances combing performance and shine while reducing frizz and flyaway.

The invention claimed is:

1. A microcapsule suspension for treating a protein-containing surface said suspension comprising droplets of a dispersed water-immiscible core phase, an aqueous continuous phase, and a wall surrounding each core phase droplet, said wall comprising the salt formed from at least one Lewis base reactant and at least one Lewis acid reactant, wherein at least one Lewis base reactant or Lewis acid reactant is amphiphilic and wherein at least one Lewis acid reactant is selected from the group consisting of proteins, protein hydrolysates, charged amino acids, and water-soluble salts of any of these.

2. The microcapsule suspension of claim 1 wherein at one Lewis acid reactant is a protein hydrolysate or waster soluble salt thereof.

3. The microcapsule suspension of claim 1 wherein at least one Lewis acid reactant is a polymer bearing carboxylic acid moieties or water-soluble salt thereof.

4. Tyre microcapsule suspension of claim 1 wherein at least one Lewis acid reactant is selected from the group consisting of e following Lewis acids and their water-soluble salts: alginic acid, arabic acid, carboxymethylcellulose, hyaluronic acid, gellan gum, pectin, and xanthan gum.

5. The microcapsule suspension of claim 1 wherein at least one Lewis base reactant is selected from the group consisting of water-soluble quaternary amines capable of forming a salt with carboxylic acid moieties present on a Lewis acid reactant.

6. The capsule suspension of claim 1 wherein at least one Lewis base reactant is a protein hydrolysate or a water-soluble salt thereof.

7. The microcapsule suspension of claim 1 wherein at least one Lewis base reactant is selected from the group consisting of the following Lewis bases, anions, and their water-soluble salts: benzalkonium, cetylpyridinium, chitosan, cocodimonium hydroxypropyl hydrolyzed keratin, cocoglucosides hydroxypropyl, hydroxypropyltrimonium hydrolyzed wheat protein, hydroxypropyl oxidized starch PG-trimonium, PEG-3 dioleylamidoethylmonium methosulfate, laurdimoniumhydroxypropyl decylglucosides, polyquaternium-10, polyquaternium-11, polyquaternium-78, polyquaternium-80, polyquaternium-81, polyquaternium-88, polyquaternium-101, quaternium-79 hydrolyzed silk protein, silicone quaternium-17, silicone quaternium-8, starch hydroxypropyltrimonium, steardimonium hydroxyethylcellulose, steardimonium hydroxypropyl panthenyl PEG-7 dimethicone, palmitamidopropyltrimonium chloride, cocodimonium hydroxyethylcellulose, and polyvinylamine.

8. The microcapsule suspension of claim 1 wherein the core phase comprises a silicone or an alkane.

9. The microcapsule suspension of claim 1 wherein the core phase comprises one or more component(s) selected from the group consisting of argan (*Argania spinosa* L.) oil, baobab (*Adansonia digitata*) seed oil, broccoli (*Brassica oleracea*) seed oil, mango (*Mangifera indica* and related) oil, moringa (*Moringa oleifera*) seed oil, palm (*Elaeis guineensis* and related) oil, tea (*Camellia sinensis*) seed oil, marula (*Sclerocarya birrea*) nut oil, shea (*Vitellaria paradoxa*) oil, tamanu (*Calophyllum inophyllum*) oil, common food oils or hydrogenated products thereof, liquid alkanes, and liquid silicones.

10. The microcapsule suspension of claim 1 wherein the core phase comprises one or more waxes selected from the group consisting of acacia (*Acacia farnesiana*) flower wax, stearin, candelilla (*Euphorbia cerifera*) wax, carnauba (*Copernicia prunifera*) wax, beeswax, paraffin, silicone wax, and ozokerite.

11. The microcapsule suspension of claim 1 wherein the core phase comprises a gellant or resin selected from the group consisting of shellac, rosin, and oil-soluble or oil-wettable polymers.

12. The microcapsule suspension of claim 10 wherein the oil-soluble or oil-wettable polymers are polyamides or copolymers of vinylpyrrolidone with long-chain olefins.

13. The microcapsule suspension of claim 1 wherein the core phase comprises a material that undergoes a phase transition at a selected temperature.

14. The microcapsule suspension of claim 12 wherein the phase transition occurs between 37° C. and 100° C.

15. The microcapsule suspension of claim 13 wherein the phase transition occurs between 45° C. and 65° C.

16. The microcapsule suspension of claim 1 wherein the core phase comprises a fluorescent material.

17. The microcapsule suspension of claim 1 wherein the aqueous continuous phase further comprises one or more suspending agents selected from the group consisting of gellan gum, alginate, carboxymethylcellulose, carrageenan, locust bean gum, starch, guar gum, pectin, arabic acid, hydroxypropyl methylcellulose, carbomer, and chemically modified versions of any of these materials, added after formation of the wall and not a part thereof.

18. The microcapsule suspension of claim 1, further comprising one or more dissolved or suspended materials selected from the group consisting of fragrances, dyes, pigments, polyvinyl alcohol, glycerin, glycols and acrylate copolymers.

19. The microcapsule suspension of claim 1 wherein the microcapsule suspension is capable of providing benefits to hair selected from the group consisting of visible repair of damage, reducing frizz and/or flyaway and/or static charge, increasing shine, promoting cascade and flow, reducing combing resistance and increasing manageability, increasing tactile softness, preventing damage, preventing stretching, reducing breakage, promoting longer hair length, preventing heat-damage, preventing signs of aging, restoring youthful qualities, prolonging youthful qualities, and preventing or repairing hair damage.

20. The microcapsule suspension of claim 1 wherein the microcapsule suspension is capable of causing reattachment of divergent cuticle scales in damaged areas of hair.

21. The microcapsule suspension of claim 1 wherein the microcapsule suspension is capable of providing heat-activated repair of hair.

22. The microcapsule suspension of claim 1 wherein the microcapsule suspension produces a tough and cohesive film or network upon drying.

23. The microcapsule suspension of claim 1 wherein the microcapsule suspension is useful for providing style, fixing, or imparting curl or structure to hair.

24. The microcapsule suspension of claim 1 wherein at least one Lewis acid reactant is a protein or a water-soluble salt thereof.

25. The microcapsule suspension of claim 1 wherein at least Erie Lewis acid reactant is a protein hydrolysate or a water-soluble salt thereof.

26. The microcapsule suspension of claim 1 wherein at least one Lewis acid reactant is a charged amino acid or a water-soluble salt thereof.

27. The microcapsule suspension of claim 1 wherein the core phase comprises acetyltributyl citrate, octylmethoxycinnamate, triglycerides, esters of tocopherol, dimethiconol behenate.

28. The microcapsule suspension of claim 1 wherein the core phase comprises triglycerides.

29. The microcapsule suspension of claim 1 wherein the core phase comprises hydrogenated castor oil/sebacic acid copolymer.

* * * * *